(12) United States Patent
Kim et al.

(10) Patent No.: US 7,056,705 B2
(45) Date of Patent: Jun. 6, 2006

(54) MULTIPLEX PCR PRIMER SET FOR HUMAN GLUCOKINASE GENE AMPLIFICATION

(75) Inventors: Mi-kyung Kim, Daejeon (KR); Yeon-su Lee, Gyeonggi-do (KR); Jung-nam Lee, Daejeon (KR)

(73) Assignee: Samsung Electronics, Co. Ltd. (KR)

( * ) Notice: Subject to any disclaimer, the term of this patent is extended or adjusted under 35 U.S.C. 154(b) by 51 days.

(21) Appl. No.: 10/265,649

(22) Filed: Oct. 7, 2002

(65) Prior Publication Data

US 2004/0009492 A1    Jan. 15, 2004

(30) Foreign Application Priority Data

Jul. 10, 2002    (KR) ................................ 2002-39989

(51) Int. Cl.
*C12P 19/34* (2006.01)
*C12Q 1/68* (2006.01)
*C07H 21/04* (2006.01)

(52) U.S. Cl. ................. 435/91.2; 536/24.33; 536/23.1; 536/24.3; 536/24.31; 536/24.32; 435/91.1; 435/6

(58) Field of Classification Search ............. 536/24.33, 536/24.3; 435/6, 91.1, 91.2, 810, 24.32
See application file for complete search history.

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 4,800,159 A | | 1/1989 | Mullis et al. |
| 5,541,060 A | * | 7/1996 | Bell et al. ...................... 435/6 |
| 5,582,989 A | | 12/1996 | Caskey et al. ................. 435/6 |
| 6,468,744 B1 | * | 10/2002 | Cronin et al. .................. 435/6 |

FOREIGN PATENT DOCUMENTS

EP    0682120    11/1995
WO    WO 9321343    10/1993

OTHER PUBLICATIONS

Boehringer Mannheim, Critical Factors for Successful PCR. Boehringer Mannheim PCR Applications Manual, Boehringer Mannheim GmbH Biochemica, Germany, 1995.*
Henegariu et al. Multiplex PCR: Critical parameters and Step-by-step protocol. Biotechniques, vol. 23, pp. 504-511, Sep. 1997.*
Saiki et al., *Primer-Directed Enzymatic Amplification of DNA With a Thermostable DNA Polymerase*, Science, vol. 239, Jan. 29, 1988, pp. 487-491.
Boutin, et al. "Routine Mutation Screening of HNF-1α and GCK genes in MODY Diagnosis: How Effective are the Techniques of DHPLC and Direct Sequencing used in Combination?" *Diabetologia* 44:775-778 (2001).
European Search Report corresponding to EP 02024499. Mailed Nov. 10, 2003.
Henegariu, et al. "Multiplex PCR: Critical Parameters and Step-by-Step Protocol" *BioTechniques* 23:504-511 (Sep. 1997).
Lehto, et al. "High Frequency of Mutations in MODY and Mitochondrial Genes in Scandinavian Patients with Familial Early-Onset Diabetes" *Diabetologia* 42:1131-1137 (1999).

* cited by examiner

*Primary Examiner*—Kenneth R. Horlick
*Assistant Examiner*—Cynthia Wilder
(74) *Attorney, Agent, or Firm*—Myers Bigel Sibley & Sajovec, P.A.

(57) ABSTRACT

The present invention provides a primer pooi for amplifying a target sequence of a human glucokinase gene including at least one set of primers or variant primers thereof, each set of primers being identified by two consecutive SEQ ID NOS, the SEQ ID NOS starting at SEQ ID NO:3 and terminating at SEQ ID NO:24 according to the present invention. A target sequence such as the human glucokinase gene may be amplified with a high specificity, a high speed, a high sensitivity and a low cost through a multiplex PCR to detect a maturity-onset of diabetes of the young (MODY) 2 associated gene.

19 Claims, 6 Drawing Sheets

Fig. 2

```
Query:  40 cccgccccgcagcgacacgggcgaccgcaagcagatctacaacatcctgagcacgctggg  99
            |||||||||  |||||||||||||||||||||  |||||||||||||||||||||||||
Sbjct:  45 cccgccccgcancgacacgggcgaccgcaagcagnactacaacatcctgagcacgctggg 104

Query  100 gctgcgaccctcgaccaccgactgcgacatcgtgcgccgcgcctgcgagagcgtgtctac 159
           ||||||||||||||||||||||||||||||||||||||||||||||||||||||||||||
Sbjct: 105 gctgcgaccctcgaccaccgactgcgacatcgtgcgccgcgcctgcgagagcgtgtctac 164

Query: 160 gcgcgctgcgcacatgtgctcggcggggctggcgggcgtcatcaaccgcatgcgcgagag 219
           ||||||||||||||||||||||||||||||||||||||||||||||||||||||||||||
Sbjct: 165 gcgcgctgcgcacatgtgctcggcggggctggcgggcgtcatcaaccgcatgcgcgagag 224

Query: 220 ccgcagcgaggacgtaatgcgcatcactgtgggcgtggatggctccgtgtacaagctgca 279
           ||||||||||||||||||||||||||||||||||||||||||||||||||||||||||||
Sbjct: 225 ccgcagcgaggacgtaatgcgcatcactgtgggcgtggatggctccgtgtacaagctgca 284

Query: 280 ccccaggtgagcctgccccgctctctccctggtaaagtggggcccaaaaagcgcgcgctc 339
           |||||||||||| |||||||||||||||||||||||||||||||||||||||||||||||
Sbjct: 285 ccccaggtgagccngcccnactctctccctggtaaagtggggcccaaaaagcgcgcgctc 344

Query: 340 caaggttccttgcggttcccaagctccaagat 371
           ||||||||||||||||||||||||||||||||
Sbjct: 345 caaggttccttgcggttcccaagctccaagat 376
```

Query: SEQ ID NO: 33

Sbjct: SEQ ID NO: 34

Fig. 5a

Exon 1c

Score = 256bits(133), Identities = 147/149(98%), Gaps = 2/149(1%)

```
Query: 64   actctcctctg-aactcgggcctcacatggcca-actgctacttggaacaaatcgccct 121
            ||||||||||| |||||||||||||||||||||  ||||||| |||||||||||||||
Sbjct: 76   actctcctctgnaactcgggcctcacatggccacactgctacttggaacaaatcgccct 135

Query: 122  tggctggcagatgtgttaacatgcccagaccaagatcccaactcccacaacccaactccc 181
            |||||||||||||||||||||||||||||||||||||||||||||||||||||||||||
Sbjct: 136  tggctggcagatgtgttaacatgcccagaccaagatcccaactcccacaacccaactccc 195

Query: 182  aggtcagatggaacctcttcttcccaggc 210
            |||||||||||||||||||||||||||||
Sbjct: 196  aggtcagatggaacctcttcttcccaggc 224
```

Query: SEQ ID NO: 35

Sbjct: SEQ ID NO: 36

Fig. 5b

Exon 7

Score = 483bits (253), Identities = 253/253 (100%)

```
Query:   1  aagcggcaggaaccaggccctactccggggcagtgcagctctcgctgacagtcccccga  60
            ||||||||||||||||||||||||||||||||||||||||||||||||||||||||||||
Sbjct: 253  aagcggcaggaaccaggccctactccggggcagtgcagctctcgctgacagtcccccga 194

Query:  61  cctccaccccaggcacgggctgcaatgcctgctacatggaggagatgcagaatgtggagc 120
            ||||||||||||||||||||||||||||||||||||||||||||||||||||||||||||
Sbjct: 193  cctccaccccaggcacgggctgcaatgcctgctacatggaggagatgcagaatgtggagc 134

Query: 121  tggtggaggggacgagggccgcatgtgcgtcaataccgagtggggcgccttcggggact 180
            ||||||||||||||||||||||||||||||||||||||||||||||||||||||||||||
Sbjct: 133  tggtggaggggacgagggccgcatgtgcgtcaataccgagtggggcgccttcggggact  74

Query: 181  ccggcgagctggacgagttcctgctggagtatgaccgcctggtggacgagagctctgcaa 240
            ||||||||||||||||||||||||||||||||||||||||||||||||||||||||||||
Sbjct:  73  ccggcgagctggacgagttcctgctggagtatgaccgcctggtggacgagagctctgcaa  14

Query: 241  accccggtcagca 253
            |||||||||||||
Sbjct:  13  accccggtcagca   1
```

Query: SEQ ID NO: 37

Sbjct: SEQ ID NO: 38

MULTIPLEX PCR PRIMER SET FOR HUMAN GLUCOKINASE GENE AMPLIFICATION

RELATED APPLICATION

This application claims the benefit of Korean Patent Application No. 2002-39989, filed Jul. 10, 2002, the disclosure of which is hereby incorporated herein by reference in its entirety as if set forth fully herein.

FIELD OF THE INVENTION

The present invention relates to a primer pool for amplifying a human glucokinase gene, and more particularly, to a primer pool for amplifying a target DNA sequence in a human glucokinase gene by multiplex PCR.

BACKGROUND OF THE INVENTION

One type of process utilized for the detection of hybridized nucleic acids involves polymerase chain reaction (PCR). The PCR process is well known in the art (U.S. Pat. Nos. 4,683,195, 4,683,202 and 4,800,159). In PCR, nucleic acid primers that are complementary to opposite strands of a nucleic acid amplification target sequence are permitted to anneal to the denatured sample. Next, DNA polymerase (typically heat stable) extends the DNA duplex from the hybridized primer. The process is then repeated to amplify the nucleic acid target. If the nucleic acid primers do not hybridize to the sample, then there is no corresponding amplified PCR product. In this case, the PCR primer acts as a hybridization probe.

In a PCR method, the amplified nucleic acid product may be detected in a number of ways, e.g., by incorporation of a labeled nucleotide into the amplified strand by using labeled primers. Primers used in PCR include, but are not limited to radioactive substances, fluorescent dyes, digoxygenin, horseradish peroxidase, alkaline phosphatase, acridinium esters, biotin and jack bean urease. PCR products made with unlabeled primers may be detected in other ways, such as electrophoretic gel separation followed by dye-based visualization.

PCR-based methods are of limited use for the detection of nucleic acids of unknown sequence. The human genome is composed of about $3 \times 10^9$ nucleotides; thus, it is difficult to isolate and analyze a specific human gene. Yet, PCR can amplify a target sequence with high speed, specificity and sensitivity by using a set of primers including primers complementary to both ends of the target sequence (Saiki et al. Science 239: 487, 1988).

PCR may be widely used in analyzing a disease-associated gene. Specifically, gene amplification by PCR may be useful for analyzing genetic variations of a disease-associated gene in the medical field. A specific disease-associated gene may be amplified using PCR, and analyzed by using a sequencing, hybridization or single strand conformational polymorphism. In analyzing genetic variations of a gene a single PCR may be enough to amplify the entire gene if the size of a target gene is small. However, if the size of a target gene is large, e.g., 1 kb or more, a single PCR may have difficulty in amplifying the entire gene. Thus, PCR may be conducted several times on several portions of the entire gene to amplify the entire gene of a large target gene. In analyzing a genetic variation of a disease-associated gene, a multiple PCR is more frequently used than a single PCR since most disease-associated genes may be 1.5 kb or larger in size.

A multiple PCR process requires a large amount of a sample, for example, a patient's DNA or blood. A multiple PCR also costs more and requires more effort and time. Thus, multiplex PCR assays have been developed to solve the above problems. A multiplex PCR simultaneously amplifies a plurality of target sequences of a gene in one reaction. Therefore, a plurality of target sequences are amplified by a single PCR using a primer pool for amplifying each target sequence.

Multiplex PCR assays are well known in the art. For example, U.S. Pat. No. 5,582,989 discloses the simultaneous detection of multiple known DNA sequence deletions. The technique disclosed therein uses a first set of probes to hybridize to the targets. Those probes are extended if the targets are present. The extension products are amplified using PCR.

A set of primers for a multiplex PCR may be able to specifically bind to a target sequence and should not interfere with each other in order to amplify the target sequence by a sufficient amount. A multiplex PCR using such a set of primers may be able to save time, effort and cost for amplifying a target sequence in comparison with a single PCR. In analyzing a genetic variation of a gene by using a DNA chip, a multiplex PCR may be useful in amplifying more than one kind of DNA sample in a reaction. Such a DNA chip may be useful in analyzing genetic variations in a gene.

It is known that a genetic variation of a human glucokinase gene, including a point mutation, causes maturity-onset diabetes in the young (MODY 2) (Matschinsky & Magnuson, in 'Molecular Pathogenesis of MODYs', Karger, 1998; U.S. Pat. No. 5,541,060; WO9321343). MODY 2, a kind of MODY disease (MODY 1, 2, 3, 4 and 5) accounts for about 10–30% of all type II diabetes mellitus cases. Thus, in analyzing a genetic variation of a human glucokinase gene, it is possible to anticipate a person's propensity to a diabetes mellitus. Therefore, in order to rapidly analyze a human glucokinase gene using, for example, a DNA chip, a set of primers for amplifying a human glucokinase gene by a multiplex PCR needs to be developed.

SUMMARY OF THE INVENTION

One of the embodiments of the present invention provides a set of primers for amplifying a target sequence of a human glucokinase gene by a multiplex PCR.

Another embodiment of the present invention provides a method for sequencing a human glucokinase gene by using a set of primers.

Other embodiments of the present invention provide kits for amplifying a target sequence.

The present invention also provides for a primer pool for amplifying target sequences of a human glucokinase gene including at least one set of primers for amplifying target sequences of a human glucokinase gene identified by SEQ ID NOS: 3 to 24 and variants thereof selected from the group consisting of:

(a) A set of primers comprising an oligonucleotide having a sequence given herein as SEQ ID NO: 3 and an oligonucleotide having a sequence given herein as SEQ ID NO: 4;

(b) A set of primers comprising an oligonucleotide having a sequence given herein as SEQ ID NO: 5 and an oligonucleotide having a sequence given herein as SEQ ID NO: 6;

(c) A set of primers comprising an oligonucleotide having a sequence given herein as SEQ ID NO: 7 and an oligonucleotide having a sequence given herein as SEQ ID NO: 8;

(d) A set of primers comprising an oligonucleotide having a sequence given herein as SEQ ID NO: 9 and an oligonucleotide having a sequence given herein as SEQ ID NO: 10;

(e) A set of primers comprising an oligonucleotide having a sequence given herein as SEQ ID NO: 11 and an oligonucleotide having a sequence given herein as SEQ ID NO: 12;

(f) A set of primers comprising an oligonucleotide having a sequence given herein as SEQ ID NO: 13 and an oligonucleotide having a sequence given herein as SEQ ID NO: 14;

(g) A set of primers comprising an oligonucleotide having a sequence given herein as SEQ ID NO: 15 and an oligonucleotide having a sequence given herein as SEQ ID NO: 16;

(h) A set of primers comprising an oligonucleotide having a sequence given herein as SEQ ID NO: 17 and an oligonucleotide having a sequence given herein as SEQ ID NO: 18;

(i) A set of primers comprising an oligonucleotide having a sequence given herein as SEQ ID NO: 19 and an oligonucleotide having a sequence given herein as SEQ ID NO: 20;

(j) A set of primers comprising an oligonucleotide having a sequence given herein as SEQ ID NO: 21 and an oligonucleotide having a sequence given herein as SEQ ID NO: 22;

(k) A set of primers comprising an oligonucleotide having a sequence given herein as SEQ ID NO: 23 and an oligonucleotide having a sequence given herein as SEQ ID NO: 24 and (l) A set of variant primers comprising a primer set according to (a) through (k) above, wherein one or both members of said set is replaced with a variant primer, said variant primer having 1 to 3 additional nucleotides joined or deleted from the 3' end, the 5' end, or both the 3' end and the 5' end thereof.

The present invention also provides a method for amplifying a target sequence of a human glucokinase gene comprising subjecting a target sequence of a human glucokinase gene to a PCR which uses the primer pool according to the present invention.

Further, the present invention provides a kit for amplifying a target sequence of a human glucokinase gene comprising the primer pool according to the present invention.

BRIEF DESCRIPTION OF THE DRAWINGS

FIG. 2 illustrates a comparison of the nucleotide sequence of a single PCR product obtained using a set of primers for amplifying exon 9 (SEQ ID NO: 33) with a known nucleotide sequence of a human glucokinase gene (SEQ ID NO: 34).

FIGS. 5a and 5b illustrate a comparison of the nucleotide sequence of a multiplex PCR product with a known sequence of a corresponding region. FIG. 5a depicts a multiplex PCR product sequence (Query, SEQ ID NO: 35) aligned with the known sequence of Exon 1c of a glucokinase gene (Sbjct, SEQ ID NO: 36). FIG. 5b demonstrates a multiplex PCR product sequence (Query, SEQ ID NO: 37) aligned with the known sequence of Exon 7 of a glucokinase gene (Sbjct, SEQ ID NO: 38).

DETAILED DESCRIPTION OF THE PREFERRED EMBODIMENTS

Figure 1:
FIG. 1 illustrates an electrophoresis result of a single PCR product and a multiplex PCR product of exons 1 to 10 of a human glucokinase gene.

To facilitate understanding of the invention, a number of terms are defined below. A "nucleic acid," as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides.

A "polynucleotide," as used herein, is a nucleic acid containing a sequence that is greater than about 100 nucleotides in length.

An "oligonucleotide," as used herein, is a short polynucleotide or a portion of a polynucleotide. An oligonucleotide typically contains a sequence of about two to about one hundred bases. The word "oligo" is sometimes used in place of the word "oligonucleotide".

A base "position" as used herein refers to the location of a given base or nucleotide residue within a nucleic acid.

A "nucleic acid of interest," as used herein, is any particular nucleic acid one desires to study in a sample.

The term "isolated", when used in relation to a nucleic acid or protein, refers to a nucleic acid sequence or protein that is identified and separated from at least one contaminant (nucleic acid or protein, respectively) with which it is ordinarily associated in its natural source. As isolated nucleic acid is different from that which is found in nature. In contrast, non-isolated nucleic acids or proteins are found in the state in which they exist in nature.

As used herein, the term "purified" or "to purify" means the result of any process which removes some contaminants from the component of interest, such as a protein or nucleic acid. The percent of a purified component is thereby increased in the sample.

The term "wild-type," as used herein, refers to a gene or gene product that has the characteristics of that gene or gene product that is most frequently observed in a population and is, thus, arbitrarily designated the "normal" or "wild-type" form of the gene. In contrast, the term "modified" or "mutant", as used herein, refers to a gene or gene product that displays modifications in sequence and/or functional properties (i.e., altered characteristics) when compared to the wild-type gene or gene product.

Nucleic acids are known to contain different types of mutations. As used herein, a "point" mutation refers to an alteration in the sequence of a nucleotide at a single base position. A "lesion", as used herein, refers to a site within a nucleic acid where one or more bases are mutated by deletion or insertion, so that the nucleic acid sequence differs from the wild-type sequence. "Insertions" or "deletions" are typically in the range of about 1 to 5 nucleic acids. The variation allowed may be experimentally determined by systematically making insertions, deletions, or substitutions of nucleic acids in a molecule using recombinant DNA techniques and assaying the resulting recombinant variants for activity.

A "single nucleotide polymorphism" or SNP, as used herein, is a variation from the most frequently occurring base at a particular nucleic acid position.

Homologous genes or alleles from different species are also known to vary in sequence. Regions of homologous genes or alleles from different species can be essentially identical in sequence. Such regions are referred to herein as "regions of identity." It is contemplated herein that a "region of substantial identity" can contain some "mismatches," where bases at the same position in the region of identity are different. This base position is referred to herein as "mismatch position." DNA molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a nucleic acid sequence, even if internal to a larger oligonucleotide or polynucleotide, also can be said to have 5'- and 3'-ends. For example, a gene sequence located within a larger chromosome sequence can still be said to have a 5'- and 3'-end.

As used herein, the 3'-terminal region of the nucleic acid probe refers to the region of the probe including nucleotides within about 10 residues from the 3'-terminal position.

In either a linear or circular DNA molecule, discrete elements are referred to as being "upstream" or "5'" relative to an element if they are bonded or would be bonded to the 5'-end of that element. Similarly, discrete elements are "downstream" or "3'" relative to an element if they are or would be bonded to the 3'-end of that element. Transcription proceeds in a 5' to 3' manner along the DNA strand. This means that RNA is made by the sequential addition of ribonucleotide-5'-triphosphates to the 3'-terminus of the growing chain (with the elimination of pyrophosphate).

As used herein, the term "target nucleic acid" or "nucleic acid target" refers to a particular nucleic acid sequence of interest. Thus, the "target" can exist in the presence of other nucleic acid molecules or within a larger nucleic acid molecule.

As used herein, the term "nucleic acid probe" refers to an oligonucleotide or polynucleotide that is capable of hybridizing to another nucleic acid of interest. A nucleic acid probe may occur naturally as in a purified restriction digest or be produced synthetically, recombinantly or by PCR amplification. As used herein, the term "nucleic acid probe" refers to the oligonucleotide or polynucleotide used in a method of the present invention. That same oligonucleotide may also be used, for example, in a PCR method as a primer for polymerization, but as used herein, that oligonucleotide would then be referred to as a "primer". Herein, oligonucleotides or polynucleotides may contain some modified linkages such as a phosphorothioate bond.

As used herein, the term "complementary" and derivatives therof are used in reference to nucleic acids (i.e., a sequence of nucleotides) related by the well-known base-pairing rules that A pairs with T and C pairs with G. For example, the sequence 5'-A-G-T-3', is complementary to the sequence 3'-T-C-A-5'. Complementarity can be "partial," in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands may have significant effects on the efficiency and strength of hybridization between nucleic acid strands as known well in the art. This may be of particular importance in detection methods that depend upon binding between nucleic acids, such as those of the invention. The term "substantially complementary" refers to any probe that can hybridize to either or both strands of the target nucleic acid sequence under conditions of low stringency as described below or, preferably, in polymerase reaction buffer (Promega, M195A) heated to 95° C. and then cooled to room temperature. As used herein, when the nucleic acid probe is referred to as partially or totally complementary to the target nucleic acid, that refers to the 3'-terminal region of the probe (i.e. within about 10 nucleotides of the 3'-terminal nucleotide position).

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence. Hybridization of such sequences as disclosed in the present invention may be carried out under conditions of reduced stringency or even stringent conditions (e.g., conditions represented by a wash stringency of 0.3 M NaCl, 0.03 M sodium citrate, 0.1% SDS at 60° C. or even 70° C. to DNA herein in a standard in situ hybridization assay. See J. Sambrook et al., Molecular Cloning, A Laboratory Manual (2d Ed. 1989)(Cold Spring Harbor Laboratory)). In general, such sequences will be at least 65% similar, 75% similar, 80% similar, 85% similar, 90% similar, or even 95% similar, or more, with the sequences given herein.

A multiplex method of this invention may be used to determine the presence or absence of a plurality of predetermined (known) nucleic acid target sequences in a nucleic acid sample. A nucleic acid target is "predetermined" in that its sequence must be known to design a probe that hybridizes with that target. However, it should be noted that a nucleic acid target sequence, as used with respect to a process of this invention, may be able to act as a reporter to signal the presence of a different nucleic acid whose presence is desired to be determined. The other nucleic acid of interest does not necessarily have to have a predetermined sequence. Furthermore, the invention may be useful in determining the identity of a base within a target in which only enough of the sequence is known to design a probe that hybridizes to that target with partial complementarity at the 3'-terminal region of the probe. Such a method utilizes an enzyme that can depolymerize the 3'-terminus of an oligonucleotide probe hybridized to the nucleic acid target sequence to release one or more identifier nucleotides whose presence or absence can then be determined as an analytical output that indicates the presence or absence of the target sequence.

A nucleic acid target sequence may be predetermined in that a nucleic acid probe is provided to be partially or totally complementary to that nucleic acid target sequence. Such nucleic acid target sequence is a portion of nucleic acid sample with which the probe hybridizes if that target sequence is present in the sample.

The present invention includes methods of admixing a sample to be assayed with a plurality of nucleic acid probes. The admixing of the first step is typically carried out under low stringency hybridizing conditions to form a hybridization composition. In such a hybridization composition, the 3'-terminal region of the nucleic acid probes (i) hybridize with partial or total complementarity to a nucleic acid target sequence that may be present in the sample; and (ii) include an identifier nucleotide in the 3'-terminal region.

The nucleic acid probe may be designed so as not hybridize with itself to form a hairpin structure in such a way as to interfere with hybridization of the 3'-terminal region of the probe to the target nucleic acid. Parameters guiding probe design are well known in the art.

The hybridization composition may be maintained under hybridizing conditions for a time period sufficient to form a treated sample that may contain a plurality of predetermined nucleic acid target sequences hybridized with their respective nucleic acid probes.

In the event that the sample to be assayed does not contain a target sequence to which a probe hybridizes, no hybridization takes place for that probe. When a method of the present invention is used to determine whether a particular target sequence is present or absent in a sample to be assayed, the resulting treated sample may not contain a substrate for the enzymes of the present invention. As a result, a 3' terminal region identifier nucleotide is not released and the analytical output is at or near background levels.

In developing a primer pool for amplifying a human glucokinase gene by a multiplex PCR, the following factors may be taken into consideration:

A primer of the primer pool should be able to bind to a target sequence of a human glucokinase gene and should not interfere with each other in order to amplify a target sequence in a sufficient amount. Each primer of a primer pool will likely have a similar melting temperature and preferably should not form a primer pair-dimer. In addition, each primer of a primer pool should not form a hairpin or primer self-dimer. A microsatellite region and a repetitive region may be excluded from a primer sequence.

A primer pool for amplifying target sequences of a human glucokinase gene includes at least one set of primers for amplifying target sequences of a human glucokinase gene identified by SEQ ID NOS: 3 to 24 and variants thereof selected from the group consisting of:

(a) A set of primers comprising an oligonucleotide having a sequence given herein as SEQ ID NO: 3 and an oligonucleotide having a sequence given herein as SEQ ID NO: 4;

(b) A set of primers comprising an oligonucleotide having a sequence given herein as SEQ ID NO: 5 and an oligonucleotide having a sequence given herein as SEQ ID NO: 6;

(c) A set of primers comprising an oligonucleotide having a sequence given herein as SEQ ID NO: 7 and an oligonucleotide having a sequence given herein as SEQ ID NO: 8;

(d) A set of primers comprising an oligonucleotide having a sequence given herein as SEQ ID NO: 9 and an oligonucleotide having a sequence given herein as SEQ ID NO: 10;

(e) A set of primers comprising an oligonucleotide having a sequence given herein as SEQ ID NO: 11 and an oligonucleotide having a sequence given herein as SEQ ID NO: 12;

(f) A set of primers comprising an oligonucleotide having a sequence given herein as SEQ ID NO: 13 and an oligonucleotide having a sequence given herein as SEQ ID NO: 14;

(g) A set of primers comprising an oligonucleotide having a sequence given herein as SEQ ID NO: 15 and an oligonucleotide having a sequence given herein as SEQ ID NO: 16;

(h) A set of primers comprising an oligonucleotide having a sequence given herein as SEQ ID NO: 17 and an oligonucleotide having a sequence given herein as SEQ ID NO: 18;

(i) A set of primers comprising an oligonucleotide having a sequence given herein as SEQ ID NO: 19 and an oligonucleotide having a sequence given herein as SEQ ID NO: 20;

(j) A set of primers comprising an oligonucleotide having a sequence given herein as SEQ ID NO: 21 and an oligonucleotide having a sequence given herein as SEQ ID NO: 22;

(k) A set of primers comprising an oligonucleotide having a sequence given herein as SEQ ID NO: 23 and an oligonucleotide having a sequence given herein as SEQ ID NO: 24; and (l) A set of variant primers comprising a primer set according to (a) through (k) above, wherein one or both members of said set is replaced with a variant primer, said variant primer having 1 to 3 additional nucleotides joined or deleted from the 3' end, the 5' end, or both the 3' end and the 5' end thereof.

The variant primer may be obtained by adding or deleting 1–3 nucleotides complementary to 1–3 terminal nucleotides of a template at least one terminal of the corresponding primer. Thus, the variant primer has the same nucleotide sequence as that of the corresponding primer except for the one terminus portion.

The present invention also includes kits for amplifying a target sequence of a human glucokinase gene according to the present invention comprises a primer pool. The kit may comprise of a conventional reagent for PCR such as a dNTP solution, DNA polymerase and buffers and the like Additionally, the present invention may be used in determining the genetic variation of a human glucokinase gene. One such variation includes MODY 2, a kind of MODY disease (MODY 1, 2, 3, 4 and 5), which accounts for about 10–30% of all type II diabetes mellitus cases. Thus, in analyzing a genetic variation of a human glucokinase gene, it is possible to anticipate a person's propensity to a diabetes mellitus. Therefore, in order to rapidly analyze a human glucokinase gene using, for example, a DNA chip, a set of primers for amplifying a human glucokinase gene by a multiplex PCR may be developed.

The present invention will be described in further detail with reference to the following examples. The following examples are for illustrative purposes and are not intended to limit the scope of the invention.

EXAMPLE 1

Preparation of Primers for Amplifying 11 Target Sequences of a Human Glucokinase Gene Primers were designed so that the size of each PCR product differs by at least 5–10 bp. In designing a set of primers for a multiplex PCR, the above described factors were taken into consideration. Furthermore, each primer was designed so as not to include four or more identical consecutive nucleotides.

HYBSIMULATOR™ (Advanced Gene Computing Technologies, Inc) was used to analyze the primer.

To improve an amplification efficiency of a PCR product, a T7 promoter sequence (SEQ ID NO:1) was added at 5' end of a forward primer and a T3 promoter sequence (SEQ ID NO:2) was added at 5' end of a reverse primer.

The sequence number and characteristics for each primer are listed in Table 1.

TABLE 1

| Primers | Sequence | Size | Tm (° C.) | PCR product (bp) |
|---|---|---|---|---|
| Exon1a-F | SEQ ID NO:3 | 22 | 69.9 | 507 |
| Exon1a-R | SEQ ID NO:4 | 22 | 71 | |
| Exon1b-F | SEQ ID NO:5 | 20 | 76.5 | 312 |
| Exon1b-R | SEQ ID NO:6 | 23 | 68.7 | |
| Exon1c-F | SEQ ID NO:7 | 21 | 71.9 | 249 |
| Exon1c-R | SEQ ID NO:8 | 21 | 69.6 | |
| Exon2-F | SEQ ID NO:9 | 21 | 74 | 365 |
| Exon2-R | SEQ ID NO:10 | 21 | 70.5 | |
| Exon3-F | SEQ ID NO:11 | 21 | 72.2 | 355 |
| Exon3-R | SEQ ID NO:12 | 21 | 72.1 | |
| Exon4-F | SEQ ID NO:13 | 22 | 70.5 | 264 |
| Exon4-R | SEQ ID NO:14 | 22 | 69.3 | |
| Exon5&6-F | SEQ ID NO:15 | 20 | 74.3 | 446 |
| Exon5&6-R | SEQ ID NO:16 | 21 | 74.2 | |
| Exon7-F | SEQ ID NO:17 | 20 | 73.7 | 370 |
| Exon7-R | SEQ ID NO:18 | 20 | 75.4 | |
| Exon8-F | SEQ ID NO:19 | 21 | 73.4 | 336 |
| Exon8-R | SEQ ID NO:20 | 22 | 69.7 | |
| Exon9-F | SEQ ID NO:21 | 21 | 71 | 410 |
| Exon9-R | SEQ ID NO:22 | 22 | 71.2 | |
| Exon10-F | SEQ ID NO:23 | 22 | 71.8 | 551 |
| Exon10-R | SEQ ID NO:24 | 22 | 68.7 | |

F: forward
R: reverse

EXAMPLE 2

Amplification of a Human Glucokinase Gene by a Single PCR

Each target sequence of a human glucokinase gene was amplified by a single PCR using each set of primers according to Example 1. The PCR was completed through initial denaturation (5 mins at 95° C.), 30 cycles of denaturation (30 secs at 95° C.), annealing (15 secs at 64° C.) and polymerization (30 secs at 72° C.), and final extension (3 mins at 72° C.). The composition of a reaction solution for the PCR was as follows:

| | |
|---|---|
| Sterilized DNase and RNase free water | 12.8 µl |
| dNTP mix (each nucleotide 2.5 mM) | 2 µl |
| 10× Taq polymerase buffer | 2 µl |
| a set of primers (each primer 10 pmol) | 2 µl |
| genomic DNA (200–1.0 µg) | 1 µl |
| Taq polymerase (5 unit/µl) | 0.2 µl |

The PCR product was analyzed by electrophoresis with 1.8% agarose gel (FIG. 1). In FIG. 1, lanes 1–11 represent PCR products corresponding to exons 1a, 1b, 1c, 2, 3, 4, 5&6, 7, 8, 9 and 10. Lane 12 represents a multiplex PCR product according to the following Example 3, and lane 13 represents a molecular marker, a 50 bp DNA ladder.

As shown in FIG. 1, a target sequence of a human glucokinase gene was amplified by a single PCR using a set of primers according to Example 1.

A single PCR product obtained by using a set of primers SEQ ID NOs: 21 and 22 was isolated and sequenced by using an automatic sequencing method. The resultant nucleotide sequence (SEQ ID NO: 33) (referred to as "query") was compared with a known sequence of a human glucokinase gene exon 9 (SEQ ID NO: 34) (referred to as "Sbjct") by DNAstar software (DNAstar Inc.) (FIG. 2). As shown in FIG. 2, the PCR product showed 98.3% sequence homology with the known sequence of a human glucokinase exon 9. A gap frequency used in the alignment was 0%.

In addition to exon 9, single PCR products of other exons were also sequenced and analyzed in the same way as described above, and each PCR product showed 95% or more homology with a known corresponding exon sequence.

EXAMPLE 3

Amplification of a Human Glucokinase Gene by a Multiplex PCR

A multiple PCR was conducted by using a set of primers according to Example 1. The reaction was conducted through initial denaturation (5 mins at 95° C.), 30 cycles of denaturation (30 secs at 95° C.), annealing (15 secs at 64° C.) and polymerization (30 secs at 72° C.), and final extension (3 mins at 72° C.). All the primers were added in a single reaction tube. The composition of the reaction solution was as follows:

| | |
|---|---|
| Sterilized DNase and RNase free water | 16.4 µl |
| dNTP mix (each nucleotide 2.5 mM) | 5 µl |
| 10× Taq polymerase buffer | 5 µl |
| a set of primers (each primer 10 pmol) | 22 µl |
| genomic DNA (200–1.0 µg) | 1 µl |
| Taq polymerase (5 unit/µl) | 0.6 µl |

The PCR product was analyzed by an electrophoresis with 1.8% agarose gel (FIG. 1 lane 11). As shown in FIG. 1, as a result of a multiplex PCR using the set of primers according to Example 1, all of the 11 target sequences (507, 312, 249, 365, 355, 264, 446, 370, 336, 410 and 551 bp) of a human glucokinase gene were amplified.

EXAMPLE 4

Figure 3A:
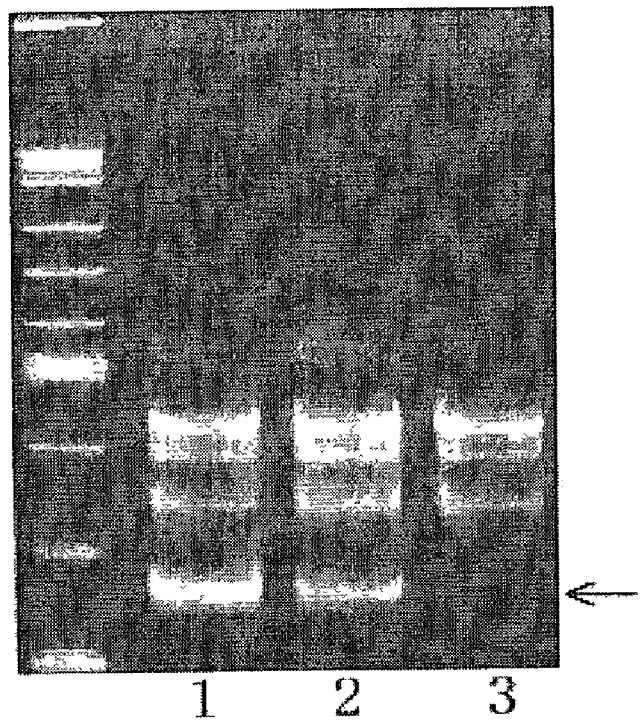
FIGS. 3a and 3b depict an electrophoresis result of a multiplex PCR product obtained using a set of variant primers.
Figure 3B:
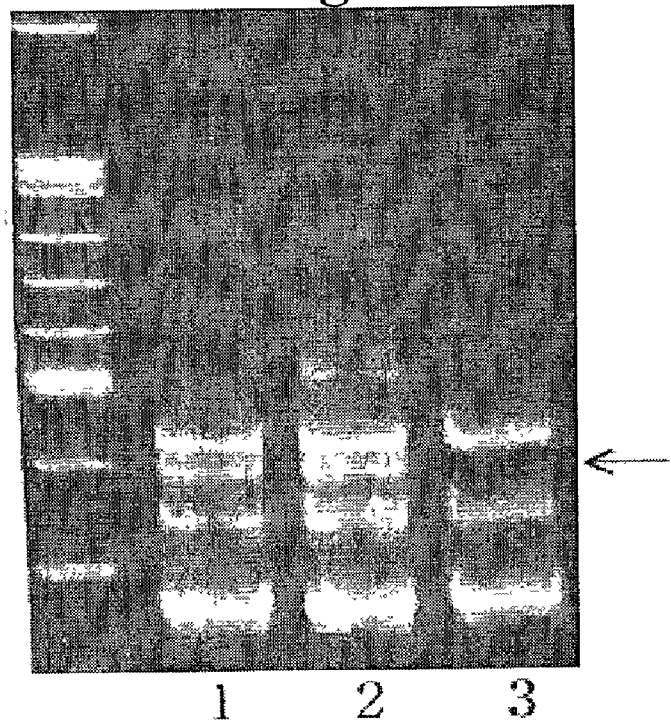

Amplification of a Human Glucokinase Gene by a Multiplex PCR Using a Set of Variant Primers A set of variant primers was synthesized by adding 3 nucleotides complementary to the template at one end of 4 sets of primers (primers sets for amplifying exons 1a, 3, 4 and 9) and by deleting 3 nucleotides at the other end of each primer. A multiplex PCR was conducted by the same method as described in the Example 1 except that one set of primers among above 4 sets of primers and the other 3 corresponding sets of primers shown in Table 1 were used (FIGS. 3a and 3b).

TABLE 2

| Primers | Sequences | |
|---|---|---|
| Exon1a-F | ~~cag~~gtcacagaagggagaggac__att__ | (SEQ ID NO: 25) |
| Exon1a-R | __tgt__tggggacaggcaagcaaac~~act~~ | (SEQ ID NO: 26) |
| Exon3-F | __taa__tatccggctcagtcacct~~ggg~~ | (SEQ ID NO: 27) |
| Exon3-R | ~~cct~~cccgtcaggactagctgg__gcc__ | (SEQ ID NO: 28) |
| Exon4-F | ~~cat~~gccagatggtcaccatggc__gtg__ | (SEQ ID NO: 29) |
| Exon4-R | __cat__ttgaaggcagagttcctct~~ggg~~ | (SEQ ID NO: 30) |
| Exon9-F | ~~gga~~ctgtcggagcgacactca__gcg__ | (SEQ ID NO: 31) |
| Exon9-R | __gaa__atcttggagcttgggaacc~~gca~~ | (SEQ ID NO: 32) |

F: forward
R: reverse
~~xxx~~: deleted nucleotides from the corresponding primer shown in Table 1.
__xxx__: added nucleotides to the corresponding primer shown in Table 1.

FIG. 3a illustrates an electrophoresis result of a multiplex PCR product obtained using a set of variant primers for exon 4 and primer sets for exons 1a, 3 and 9 shown in Table 1. FIG. 3b illustrates an electrophoresis result of a multiplex PCR product obtained using a set of variant primers for exon 9 and primer sets for exons 1a, 3 and 4 shown in Table 1 (an electrophoresis result of a multiplex PCR product obtained using a set of variant primers for exons 1a and 3 is not shown). In FIGS. 3a and 3b, the first lane from the left is a molecular marker, a 50 bp DNA ladder, lane 2 is a multiplex PCR result obtained by using a set of primers shown in Table 1, lane 2 is a multiplex PCR result obtained by using a set of variant primers for exons 4 and 9 shown in Table 2 and lane 3 is a multiplex PCR result obtained by using above 3 sets of primers without a set of primers for exon 4 or 9.

As shown in FIGS. 3a and 3b, a corresponding target sequence of a gene was amplified by a multiplex PCR using a set of variant primers.

EXAMPLE 5

Identification of a Multiplex PCR Product Through a Southern Blotting Analysis

PCR products amplified according to Examples 2 and 3 were electrophoresed with 1.8% agarose gel (FIG. 1). The gel was added into a denaturation solution (0.5N NaOH+ 1.5M NaCl) with stirring for 15 minutes to denature the double-stranded DNA. After performing the denaturation process twice, repeating two times, the gel was washed with distilled water, then the gel was added into a neutralization solution (3M NaCl containing 0.5M Tris-HCl, pH 7.5) for 15 minutes with gentle stirring to neutralize the gel. After performing the neutralization procedure twice, a DNA within the gel was transferred to a nylon membrane by reacting the gel with the nylon membrane in 20×SSC solution for 12.5 hours. The DNA was cross-linked to the nylon membrane by reacting for 30 minutes at 120° C., and the membrane was washed for 1–2 minutes and dried.

The obtained DNA attached-membrane was then put into 20 ml of a hybridization solution for about 2 hours at 62° C. for prehybridization and the solution was discarded. The DNA attached-membrane and 5 pmol/ml of DIG (digoxigenin) labeled probe were added into 10 ml of a fresh hybridization solution bag and reacted for about 12 hours at 62° C. During the reaction, the DIG labeled probe hybridized to a complementary region of a gene. After the reaction, the membrane was washed twice with 2× washing solution (2×SSC+ 0.1% SDS) for 5 minutes at room temperature, and washed twice with 0.5× washing solution (0.5×SSC+0.1% SDS) for 15 minutes at 62° C.

Figure 4:
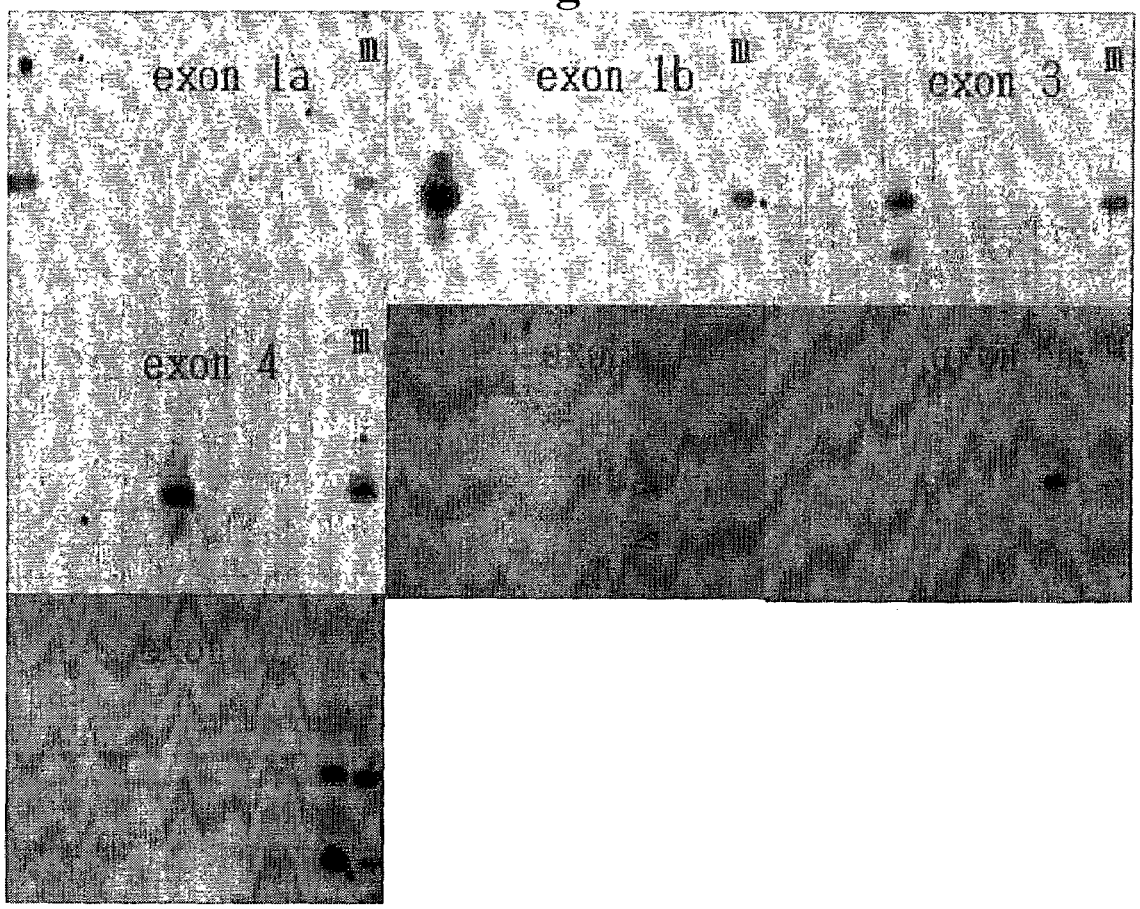
FIG. 4 is a photograph for illustrating a Southern blotting result of a single PCR and a multiplex PCR obtained using each primer set for amplifying each exon as a probe.

The membrane was introduced into 20 ml of a blocking solution for about 30–60 minutes, then the membrane was reacted with anti-DIG antibody in 20 ml of the blocking solution containing 1 μl of an alkaline phosphatase-conjugated sheep anti-DIG antibody (Roche) for about 30 minutes. The membrane was then washed twice with a washing solution (100 mM maleic acid, 150 mM NaCl, pH 7.5 at room temperature, 0.3% Tween 20) for about 15 minutes. To confirm the hybridization between DNA and a probe on the membrane, an alkaline phosphatase substrate, CDP-Star was mixed with a detection buffer solution with a ratio of 1:100 and the membrane was treated with this solution for about 5 minutes, and an X-ray film was exposed to this membrane. The film was developed to confirm the position of a probe (FIG. 4). As shown in FIG. 4, exon 1a, exon 1b, exon 3, exon 4, exon 8, exon 9 and exon 10 represent a single PCR product of a corresponding exon respectively, and m represents a multiplex PCR product.

As shown in FIG. 4, the probe hybridized to a single PCR product and a multiplex PCR product at the same position, which means that the amplified product is substantially identical.

EXAMPLE 6

Identification of a Multiplex PCR Product Through a Sequencing Analysis

A sequencing PCR was conducted by using a multiplex PCR product prepared according to Example 3 as a template and respective corresponding primers for amplification as a sequencing primer. Among PCR results, FIG. 5 represents a sequencing PCR result obtained by using primers for amplifying exon 1c (FIG. 5a) and exon 7 (FIG. 5b) as sequencing primers. FIGS. 5a and 5b illustrate a comparison of the sequencing result with corresponding known exon sequences of a human glucokinase gene. As shown in FIGS. 5a and 5b, the sequences of human glucokinase gene exon 1c and exon 7 obtained by the present multiplex PCR have a homology of 95% or more.

The primer pool for amplifying a human glucokinase gene of the present invention is effective in amplifying a corresponding gene by a multiplex PCR. Particularly, the primer pool for amplifying a gene by a multiplex PCR is useful for an analysis of a disease-associated gene by using a DNA chip since the multiplex PCR requires relatively a reduced number of samples.

The primer pool for amplifying a human glucokinase gene of the present invention may then be applied to a kit for amplifying or sequencing a human glucokinase gene.

In the specification, there have been disclosed typical preferred embodiments of the invention and, although specific terms are employed, they are used in a generic and descriptive sense only and not for purposes of limitation of the scope of the invention, that being set forth in the following claims.

What is claimed is:

1. A primer pool for amplifying eleven target sequences of a human glucokinase gene comprising:
   a) A set of primers comprising an oligonucleotide having a sequence given herein as SEQ ID NO: 3 or a variant oligonucleotide thereof and an oligonucleotide having a sequence given herein as SEQ ID NO: 4 or a variant oligonucleotide thereof;
   b) A set of primers comprising an oligonucleotide having a sequence given herein as SEQ ID NO: 5 or a variant oligonucleotide thereof and an oligonucleotide having a sequence given herein as SEQ ID NO: 6 or a variant oligonucleotide thereof;
   c) A set of primers comprising an oligonucleotide having a sequence given herein as SEQ ID NO: 7 or a variant oligonucleotide thereof and an oligonucleotide having a sequence given herein as SEQ ID NO: 8 or a variant oligonucleotide thereof;
   d) A set of primers comprising an oligonucleotide having a sequence given herein as SEQ ID NO: 9 or a variant oligonucleotide thereof and an oligonucleotide having a sequence given herein as SEQ ID NO: 10 or a variant oligonucleotide thereof;
   e) A set of primers comprising an oligonucleotide having a sequence given herein as SEQ ID NO: 11 or a variant oligonucleotide thereof and an oligonucleotide having a sequence given herein as SEQ ID NO: 12 or a variant oligonucleotide thereof;
   f) A set of primers comprising an oligonucleotide having a sequence given herein as SEQ ID NO: 13 or a variant oligonucleotide thereof and an oligonucleotide having a sequence given herein as SEQ ID NO: 14 or a variant oligonucleotide thereof;
   g) A set of primers comprising an oligonucleotide having a sequence given herein as SEQ ID NO: 15 or a variant oligonucleotide thereof and an oligonucleotide having a sequence given herein as SEQ ID NO: 16 or a variant oligonucleotide thereof;
   h) A set of primers comprising an oligonucleotide having a sequence given herein as SEQ ID NO: 17 or a variant oligonucleotide thereof and an oligonucleotide having a sequence given herein as SEQ ID NO: 18 or a variant oligonucleotide thereof;
   i) A set of primers comprising an oligonucleotide having a sequence given herein as SEQ ID NO: 19 or a variant oligonucleotide thereof and an oligonucleotide having a sequence given herein as SEQ ID NO: 20 or a variant oligonucleotide thereof;
   j) A set of primers comprising an oligonucleotide having a sequence given herein as SEQ ID NO: 21 or a variant oligonucleotide thereof and an oligonucleotide having a sequence given herein as SEQ ID NO: 22 or a variant oligonucleotide thereof; and
   k) A set of primers comprising an oligonucleotide having a sequence given herein as SEQ ID NO: 23 or a variant oligonucleotide thereof and an oligonucleotide having a sequence given herein as SEQ ID NO: 24 or a variant oligonucleotide thereof,
      wherein said variant oligonucleotide is an oligonucleotide having 1 to 3 additional nucleotides joined or deleted from the 3' end, the 5' end, or both the 3' end and the 5' end of the corresponding oligonucleotide.

2. The primer pool of claim 1, wherein at least one of the primers includes a T7 promoter sequence or a T3 promoter sequence at its 5' terminal.

3. The primer pooi of claim 1, wherein at least one of primers identified by SEQ ID NOS: 3, 5, 7, 9, 11, 13, 15, 17, 19,21 and 23 includes a T7 promoter sequence at its 5' terminal and at least one of primers identified by SEQ ID NOS: 4, 6, 8, 10, 12, 14, 16, 18, 20, 22 and 24 includes a T3 promoter sequence at its 5' terminal.

4. A method for amplifying eleven target sequences of a human glucokinase gene comprising subjecting the eleven target sequences of a human glucokinase gene to a PCR using a primer pooi comprising:
   a) A set of primers comprising an oligonucleotide having a sequence given herein as SEQ ID NO: 3 or a variant oligonucleotide thereof and an oligonucleotide having a sequence given herein as SEQ ID NO: 4 or a variant oligonucleotide thereof;
   b) A set of primers comprising an oligonucleotide having a sequence given herein as SEQ ID NO: 5 or a variant oligonucleotide thereof and an oligonucleotide having a sequence given herein as SEQ ID NO: 6 or a variant oligonucleotide thereof;
   c) A set of primers comprising an oligonucleotide having a sequence given herein as SEQ ID NO: 7 or a variant oligonucleotide thereof and an oligonucleotide having a sequence given herein as SEQ ID NO: 8 or a variant oligonucleotide thereof;
   d) A set of primers comprising an oligonucleotide having a sequence given herein as SEQ ID NO: 9 or a variant oligonucleotide thereof and an oligonucleotide having a sequence given herein as SEQ ID NO: 10 or a variant oligonucleotide thereof;
   e) A set of primers comprising an oligonucleotide having a sequence given herein as SEQ ID NO: 11 or a variant oligonucleotide thereof and an oligonucleotide having a sequence given herein as SEQ ID NO: 12 or a variant oligonucleotide thereof;
   f) A set of primers comprising an oligonucleotide having a sequence given herein as SEQ ID NO: 13 or a variant oligonucleotide thereof and an oligonucleotide having a sequence given herein as SEQ ID NO: 14 or a variant oligonucleotide thereof;
   g) A set of primers comprising an oligonucleotide having a sequence given herein as SEQ ID NO: 15 or a variant oligonucleotide thereof and an oligonucleotide having a sequence given herein as SEQ ID NO: 16 or a variant oligonucleotide thereof;
   h) A set of primers comprising an oligonucleotide having a sequence given herein as SEQ ID NO: 17 or a variant oligonucleotide thereof and an oligonucleotide having a sequence given herein as SEQ ID NO: 18 or a variant oligonucleotide thereof;
   i) A set of primers comprising an oligonucleotide having a sequence given herein as SEQ ID NO: 19 or a variant oligonucleotide thereof and an oligonucleotide having a sequence given herein as SEQ ID NO: 20 or a variant oligonucleotide thereof;
   j) A set of primers comprising an oligonucleotide having a sequence given herein as SEQ ID NO: 21 or a variant oligonucleotide thereof and an oligonucleotide having a sequence given herein as SEQ ID NO: 22 or a variant oligonucleotide thereof; and
   k) A set of primers comprising an oligonucleotide having a sequence given herein as SEQ ID NO: 23 or a variant oligonucleotide thereof and an oligonucleotide having a sequence given herein as SEQ ID NO: 24 or a variant oligonucleotide thereof,
wherein said variant oligonucleotide is an oligonucleotide having 1 to 3 additional nucleotides joined or deleted from the 3' end, the 5' end, or both the 3' end and the 5' end of the corresponding oligonucleotide.

5. The method according to claim 4, wherein at least one of the primers includes a T7 promoter sequence or a T3 promoter sequence at its 5' terminal.

6. The method according to claim 4, wherein at least one of primers identified by SEQ ID NOS: 3, 5, 7, 9, 11, 13, 15, 17, 19, 21 and 23 includes a T7 promoter sequence at its 5' terminal and at least one of primers identified by SEQ ID NOS: 4, 6, 8, 10, 12, 14, 16, 18, 20, 22 and 24 includes a T3 promoter sequence at its 5' terminal.

7. The method of claim 4, wherein the PCR is conducted in the conditions of initial denaturation for 1–5 min at 90° C.–98° C., denaturation for 10 sec to 1 min at 90° C.–98° C., annealing for 5 sec–3 min at 60° C.–65° C., polymerization for 5 sec–5 min at 70° C.–75° C. and final extension for 1 min to 10 min at 70° C.–75° C.

8. A method for sequencing eleven target nucleotide sequences of a human glucokinase gene by using a primer pool comprising:
   a) A set of primers comprising an oligonucleotide having a sequence given herein as SEQ ID NO: 3 or a variant oligonucleotide thereof and an oligonucleotide having a sequence given herein as SEQ ID NO: 4 or a variant oligonucleotide thereof;
   b) A set of primers comprising an oligonucleotide having a sequence given herein as SEQ ID NO: 5 or a variant oligonucleotide thereof and an oligonucleotide having a sequence given herein as SEQ ID NO: 6 or a variant oligonucleotide thereof
   c) A set of primers comprising an oligonucleotide having a sequence given herein as SEQ ID NO: 7 or a variant oligonucleotide thereof and an oligonucleotide having a sequence given herein as SEQ ID NO: 8 or a variant oligonucleotide thereof
   d) A set of primers comprising an oligonucleotide having a sequence given herein as SEQ ID NO: 9 or a variant oligonucleotide thereof and an oligonucleotide having a sequence given herein as SEQ ID NO: 10 or a variant oligonucleotide thereof
   e) A set of primers comprising an oligonucleotide having a sequence given herein as SEQ ID NO: 11 or a variant oligonucleotide thereof and an oligonucleotide having a sequence given herein as SEQ ID NO: 12 or a variant oligonucleotide thereof;
   f) A set of primers comprising an oligonucleotide having a sequence given herein as SEQ ID NO: 13 or a variant oligonucleotide thereof and an oligonucleotide having a sequence given herein as SEQ ID NO: 14 or a variant oligonucleotide thereof;
   g) A set of primers comprising an oligonucleotide having a sequence given herein as SEQ ID NO: 15 or a variant oligonucleotide thereof and an oligonucleotide having a sequence given herein as SEQ ID NO: 16 or a variant oligonucleotide thereof;
   h) A set of primers comprising an oligonucleotide having a sequence given herein as SEQ ID NO: 17 or a variant oligonucleotide thereof and an oligonucleotide having a sequence given herein as SEQ ID NO: 18 or a variant oligonucleotide thereof;
   i) A set of primers comprising an oligonucleotide having a sequence given herein as SEQ ID NO: 19 or a variant oligonucleotide thereof and an oligonucleotide having a sequence given herein as SEQ ID NO: 20 or a variant oligonucleotide thereof;

j) A set of primers comprising an oligonucleotide having a sequence given herein as SEQ ID NO: 21 or a variant oligonucleotide thereof and an oligonucleotide having a sequence given herein as SEQ ID NO: 22 or a variant oligonucleotide thereof; and k) A set of primers comprising an oligonucleotide having a sequence given herein as SEQ ID NO: 23 or a variant oligonucleotide thereof and an oligonucleotide having a sequence given herein as SEQ ID NO: 24 or a variant oligonucleotide thereof, wherein said variant oligonucleotide is an oligonucleotide having 1 to 3 additional nucleotides joined or deleted from the 3' end, the 5' end, or both the 3' end and the 5' end of the corresponding oligonucleotide.

9. The method according to claim 8, wherein at least one of the primers includes a T7 promoter sequence or a T3 promoter sequence at its 5' terminal.

10. The method according to claim 8, wherein at least one of primers identified by SEQ ID NOS: 3, 5, 7, 9, 11, 13, 15, 17, 19, 21 and 23 includes a T7 promoter sequence at its 5' terminal and at least one of primers identified by SEQ ID NOS: 4, 6, 8, 10, 12, 14, 16, 18, 20, 22 and 24 includes a T3 promoter sequence at its 5' terminal.

11. A kit for amplifying eleven target sequences of a human glucokinase gene comprising the primer pool of claim 1.

12. The kit of claim 11, wherein at least one of the primers includes a T7 promoter sequence or a T3 promoter sequence at its 5' terminal.

13. The kit of claim 11, wherein at least one of primers identified by SEQ ID NOS: 3, 5, 7, 9, 11, 13, 15, 17, 19, 21 and 23 includes a T7 promoter sequence at its 5' terminal and at least one of primers identified by SEQ ID NOS: 4, 6, 8, 10, 12, 14, 16, 18, 20, 22 and 24 includes a T3 promoter sequence at its 5' terminal.

14. A method of characterizing a test sample for diabetes comprising amplifying eleven target sequences of a human glucokinase gene using a primer pool comprising:

a) A set of primers comprising an oligonucleotide having a sequence given herein as SEQ ID NO: 3 or a variant oligonucleotide thereof and an oligonucleotide having a sequence given herein as SEQ ID NO: 4 or a variant oligonucleotide thereof;

b) A set of primers comprising an oligonucleotide having a sequence given herein as SEQ ID NO: 5 or a variant oligonucleotide thereof and an oligonucleotide having a sequence given herein as SEQ ID NO: 6 or a variant oligonucleotide thereof;

c) A set of primers comprising an oligonucleotide having a sequence given herein as SEQ ID NO: 7 or a variant oligonucleotide thereof and an oligonucleotide having a sequence given herein as SEQ ID NO: 8 or a variant oligonucleotide thereof;

d) A set of primers comprising an oligonucleotide having a sequence given herein as SEQ ID NO: 9 or a variant oligonucleotide thereof and an oligonucleotide having a sequence given herein as SEQ ID NO: 10 or a variant oligonucleotide thereof;

e) A set of primers comprising an oligonucleotide having a sequence given herein as SEQ ID NO: 11 or a variant oligonucleotide thereof and an oligonucleotide having a sequence given herein as SEQ ID NO: 12 or a variant oligonucleotide thereof, f) A set of primers comprising an oligonucleotide having a sequence given herein as SEQ ID NO: 13 or a variant oligonucleotide thereof and an oligonucleotide having a sequence given herein as SEQ ID NO: 14 or a variant oligonucleotide thereof;

g) A set of primers comprising an oligonucleotide having a sequence given herein as SEQ ID NO: 15 or a variant oligonucleotide thereof and an oligonucleotide having a sequence given herein as SEQ ID NO: 16 or a variant oligonucleotide thereof;

h) A set of primers comprising an oligonucleotide having a sequence given herein as SEQ ID NO: 17 or a variant oligonucleotide thereof and an oligonucleotide having a sequence given herein as SEQ ID NO: 18 or a variant oligonucleotide thereof;

i) A set of primers comprising an oligonucleotide having a sequence given herein as SEQ ID NO: 19 or a variant oligonucleotide thereof and an oligonucleotide having a sequence given herein as SEQ ID NO: 20 or a variant oligonucleotide thereof j) A set of primers comprising an oligonucleotide having a sequence given herein as SEQ ID NO: 21 or a variant oligonucleotide thereof and an oligonucleotide having a sequence given herein as SEQ ID NO: 22 or a variant oligonucleotide thereof and k) A set of primers comprising an oligonucleotide having a sequence given herein as SEQ ID NO: 23 or a variant oligonucleotide thereof and an oligonucleotide having a sequence given herein as SEQ ID NO: 24 or a variant oligonucleotide thereof, wherein said variant oligonucleotide is an oligonucleotide having 1 to 3 additional nucleotides joined or deleted from the 3' end, the 5' end, or both the 3' end and the 5' end of the corresponding oligonucleotide.

15. The method according to claim 14, comprising further adding a label to the nucleic acid sequences in said sample before hybridizing them to oligonucleotides in a microchip.

16. The method according to claim 14, wherein said diabetes is Maturity onset diabetes in the young type 2 (MODY 2).

17. The method according to claim 14, wherein said characterizing a test sample comprises testing for deletions, mutations and polymorphisms.

18. The method according to claim 14, wherein at least one of the primers includes a T7 promoter sequence or a T3 promoter sequence at its 5' terminal.

19. The method according to claim 14, wherein at least one of primers identified by SEQ ID NOS: 3, 5, 7, 9, 11, 13, 15, 17, 19, 21 and 23 includes a T7 promoter sequence at its 5' terminal and at least one of primers identified by SEQ ID NOS: 4, 6, 8, 10, 12, 14, 16, 18, 20, 22 and 24 includes a T3 promoter sequence at its 5' terminal.

* * * * *

UNITED STATES PATENT AND TRADEMARK OFFICE
CERTIFICATE OF CORRECTION

| | | |
|---|---|---|
| PATENT NO. | : 7,056,705 B2 | Page 1 of 1 |
| APPLICATION NO. | : 10/265649 | |
| DATED | : June 6, 2006 | |
| INVENTOR(S) | : Kim et al. | |

It is certified that error appears in the above-identified patent and that said Letters Patent is hereby corrected as shown below:

On the Title Page,
Section 57, Line 1 should read -- The present invention provides a primer pool for amplifying --

Column 25,
Line 39 should read -- 1. A primer pool for amplifying eleven target sequences of --

Column 27,
Line 6 should read -- 3. The primer pool of claim 1, wherein at least one of --

Line 15 should read -- using a primer pool comprising: --

Signed and Sealed this

Twenty-first Day of November, 2006

JON W. DUDAS
*Director of the United States Patent and Trademark Office*

SEQUENCE LISTING

<160> NUMBER OF SEQ ID NOS: 38

<210> SEQ ID NO 1
<211> LENGTH: 20
<212> TYPE: DNA
<213> ORGANISM: Artificial sequence
<220> FEATURE:
<223> OTHER INFORMATION: Bacteriophage T7 promoter sequences

<400> SEQUENCE: 1
taatacgact cactataggg                                          20

<210> SEQ ID NO 2
<211> LENGTH: 19
<212> TYPE: DNA
<213> ORGANISM: Artificial sequence
<220> FEATURE:
<223> OTHER INFORMATION: Bacteriophage T3 promoter sequences

<400> SEQUENCE: 2
gtaaccctca ctaaaggga                                           19

<210> SEQ ID NO 3
<211> LENGTH: 22
<212> TYPE: DNA
<213> ORGANISM: Artificial sequence
<220> FEATURE:
<223> OTHER INFORMATION: Exon 1a forward primer

<400> SEQUENCE: 3
caggtcacag aagggagagg ac                                       22

<210> SEQ ID NO 4
<211> LENGTH: 22
<212> TYPE: DNA
<213> ORGANISM: Artificial sequence
<220> FEATURE:
<223> OTHER INFORMATION: Exon 1a reverse primer

<400> SEQUENCE: 4
tggggacagg caagcaaaca ct                                       22

<210> SEQ ID NO 5
<211> LENGTH: 20
<212> TYPE: DNA
<213> ORGANISM: Artificial sequence
<220> FEATURE:
<223> OTHER INFORMATION: Exon 1b forward primer

<400> SEQUENCE: 5
agcagccgcc agctgagccc                                          20

<210> SEQ ID NO 6
<211> LENGTH: 23
<212> TYPE: DNA
<213> ORGANISM: Artificial sequence
<220> FEATURE:
<223> OTHER INFORMATION: Exon 1b reverse primer

<400> SEQUENCE: 6
ctcccagtgc aaagtcccta act                                      23

<210> SEQ ID NO 7
<211> LENGTH: 21

```
<212> TYPE: DNA
<213> ORGANISM: Artificial sequence
<220> FEATURE:
<223> OTHER INFORMATION: Exon 1c forward primer

<400> SEQUENCE: 7
ccaggccagt ggccttaagg a                                              21

<210> SEQ ID NO 8
<211> LENGTH: 21
<212> TYPE: DNA
<213> ORGANISM: Artificial sequence
<220> FEATURE:
<223> OTHER INFORMATION: Exon 1c reverse primer

<400> SEQUENCE: 8
gcctgggaag aagaggttcc a                                              21

<210> SEQ ID NO 9
<211> LENGTH: 21
<212> TYPE: DNA
<213> ORGANISM: Artificial sequence
<220> FEATURE:
<223> OTHER INFORMATION: Exon 2 forward primer

<400> SEQUENCE: 9
gccctcggtg tgcagatgcc t                                              21

<210> SEQ ID NO 10
<211> LENGTH: 21
<212> TYPE: DNA
<213> ORGANISM: Artificial sequence
<220> FEATURE:
<223> OTHER INFORMATION: Exon 2 reverse primer

<400> SEQUENCE: 10
ggtgcttctc ccagctaggc t                                              21

<210> SEQ ID NO 11
<211> LENGTH: 21
<212> TYPE: DNA
<213> ORGANISM: Artificial sequence
<220> FEATURE:
<223> OTHER INFORMATION: Exon 3 forward primer

<400> SEQUENCE: 11
tatccggctc agtcacctgg g                                              21

<210> SEQ ID NO 12
<211> LENGTH: 21
<212> TYPE: DNA
<213> ORGANISM: Artificial sequence
<220> FEATURE:
<223> OTHER INFORMATION: Exon 3 reverse primer

<400> SEQUENCE: 12
cctcccgtca ggactagctg g                                              21

<210> SEQ ID NO 13
<211> LENGTH: 22
<212> TYPE: DNA
<213> ORGANISM: Artificial sequence
<220> FEATURE:
<223> OTHER INFORMATION: Exon 4 forward primer

<400> SEQUENCE: 13
```
catgccagat ggtcaccatg gc          22

<210> SEQ ID NO 14
<211> LENGTH: 22
<212> TYPE: DNA
<213> ORGANISM: Artificial sequence
<220> FEATURE:
<223> OTHER INFORMATION: Exon 4 reverse primer

<400> SEQUENCE: 14
ttgaaggcag agttcctctg gg          22

<210> SEQ ID NO 15
<211> LENGTH: 20
<212> TYPE: DNA
<213> ORGANISM: Artificial sequence
<220> FEATURE:
<223> OTHER INFORMATION: Exon 5 and 6 forward primer

<400> SEQUENCE: 15
gccctagcac cctgcctcca          20

<210> SEQ ID NO 16
<211> LENGTH: 21
<212> TYPE: DNA
<213> ORGANISM: Artificial sequence
<220> FEATURE:
<223> OTHER INFORMATION: Exon 5 and 6 reverse primer

<400> SEQUENCE: 16
agcctcggca gtctggaagg g          21

<210> SEQ ID NO 17
<211> LENGTH: 20
<212> TYPE: DNA
<213> ORGANISM: Artificial sequence
<220> FEATURE:
<223> OTHER INFORMATION: Exon 7 forward primer

<400> SEQUENCE: 17
ggaagcggca ggaaccaggc          20

<210> SEQ ID NO 18
<211> LENGTH: 20
<212> TYPE: DNA
<213> ORGANISM: Artificial sequence
<220> FEATURE:
<223> OTHER INFORMATION: Exon 7 reverse primer

<400> SEQUENCE: 18
atggcccggc tcccatctgc          20

<210> SEQ ID NO 19
<211> LENGTH: 21
<212> TYPE: DNA
<213> ORGANISM: Artificial sequence
<220> FEATURE:
<223> OTHER INFORMATION: Exon 8 forward primer

<400> SEQUENCE: 19
cccggcttcc acctgcatga g          21

<210> SEQ ID NO 20
<211> LENGTH: 22
<212> TYPE: DNA
<213> ORGANISM: Artificial sequence

```
<220> FEATURE:
<223> OTHER INFORMATION: Exon 8 reverse primer

<400> SEQUENCE: 20
ctgagaccaa gtctgcagtg cc                                           22

<210> SEQ ID NO 21
<211> LENGTH: 21
<212> TYPE: DNA
<213> ORGANISM: Artificial sequence
<220> FEATURE:
<223> OTHER INFORMATION: Exon 9 forward primer

<400> SEQUENCE: 21
ggactgtcgg agcgacactc a                                            21

<210> SEQ ID NO 22
<211> LENGTH: 22
<212> TYPE: DNA
<213> ORGANISM: Artificial sequence
<220> FEATURE:
<223> OTHER INFORMATION: Exon 9 reverse primer

<400> SEQUENCE: 22
atcttggagc ttgggaaccg ca                                           22

<210> SEQ ID NO 23
<211> LENGTH: 22
<212> TYPE: DNA
<213> ORGANISM: Artificial sequence
<220> FEATURE:
<223> OTHER INFORMATION: Exon 10 forward primer

<400> SEQUENCE: 23
agggcgcccg gtaatgaatg tg                                           22

<210> SEQ ID NO 24
<211> LENGTH: 22
<212> TYPE: DNA
<213> ORGANISM: Artificial sequence
<220> FEATURE:
<223> OTHER INFORMATION: Exon 10 reverse primer

<400> SEQUENCE: 24
aagtcctgag tgagcaactc cc                                           22

<210> SEQ ID NO 25
<211> LENGTH: 22
<212> TYPE: DNA
<213> ORGANISM: Artificial sequence
<220> FEATURE:
<223> OTHER INFORMATION: Exon 1a variant forward primer

<400> SEQUENCE: 25
gtcacagaag ggagaggaca tt                                           22

<210> SEQ ID NO 26
<211> LENGTH: 22
<212> TYPE: DNA
<213> ORGANISM: Artificial sequence
<220> FEATURE:
<223> OTHER INFORMATION: Exon 1a variant reverse primer

<400> SEQUENCE: 26
tgttggggac aggcaagcaa ac                                           22
```

```
<210> SEQ ID NO 27
<211> LENGTH: 21
<212> TYPE: DNA
<213> ORGANISM: Artificial sequence
<220> FEATURE:
<223> OTHER INFORMATION: Exon 3 variant forward primer

<400> SEQUENCE: 27
taatatccgg ctcagtcacc t                                              21

<210> SEQ ID NO 28
<211> LENGTH: 21
<212> TYPE: DNA
<213> ORGANISM: Artificial sequence
<220> FEATURE:
<223> OTHER INFORMATION: Exon 3 variant reverse primer

<400> SEQUENCE: 28
cccgtcagga ctagctgggc c                                              21

<210> SEQ ID NO 29
<211> LENGTH: 22
<212> TYPE: DNA
<213> ORGANISM: Artificial sequence
<220> FEATURE:
<223> OTHER INFORMATION: Exon 4 variant forward primer

<400> SEQUENCE: 29
gccagatggt caccatggcg tg                                             22

<210> SEQ ID NO 30
<211> LENGTH: 22
<212> TYPE: DNA
<213> ORGANISM: Artificial sequence
<220> FEATURE:
<223> OTHER INFORMATION: Exon 4 variant reverse primer

<400> SEQUENCE: 30
catttgaagg cagagttcct ct                                             22

<210> SEQ ID NO 31
<211> LENGTH: 21
<212> TYPE: DNA
<213> ORGANISM: Artificial sequence
<220> FEATURE:
<223> OTHER INFORMATION: Exon 9 variant forward primer

<400> SEQUENCE: 31
ctgtcggagc gacactcagc g                                              21

<210> SEQ ID NO 32
<211> LENGTH: 22
<212> TYPE: DNA
<213> ORGANISM: Artificial sequence
<220> FEATURE:
<223> OTHER INFORMATION: Exon 9 variant reverse primer

<400> SEQUENCE: 32
gaaatcttgg agcttgggaa cc                                             22

<210> SEQ ID NO 33
<211> LENGTH: 333
<212> TYPE: DNA
<213> ORGANISM: Artificial sequence
<220> FEATURE:
<223> OTHER INFORMATION: Exon 9 PCR amplification product
```

<400> SEQUENCE: 33

| tcccgccccg | cagcgacacg | ggcgaccgca | agcagatcta | caacatcctg | agcacgctgg | 60 |
| ggctgcgacc | ctcgaccacc | gactgcgaca | tcgtgcgccg | cgcctgcgag | agcgtgtcta | 120 |
| cgcgcgctgc | gcacatgtgc | tcggcggggc | tggcgggcgt | catcaaccgc | atgcgcgaga | 180 |
| gccgcagcga | ggacgtaatg | cgcatcactg | tgggcgtgga | tggctccgtg | tacaagctgc | 240 |
| accccaggtg | agcctgcccc | gctctctccc | tggtaaagtg | gggcccaaaa | agcgcgcgct | 300 |
| ccaaggttcc | ttgcggttcc | caagctccaa | gat | | | 333 |

<210> SEQ ID NO 34
<211> LENGTH: 333
<212> TYPE: DNA
<213> ORGANISM: Homo sapiens
<220> FEATURE:
<221> NAME/KEY: misc_feature
<222> LOCATION: (13)..(13)
<223> OTHER INFORMATION: unknown nucleotide
<220> FEATURE:
<221> NAME/KEY: misc_feature
<222> LOCATION: (36)..(36)
<223> OTHER INFORMATION: unknown nucleotide
<220> FEATURE:
<221> NAME/KEY: misc_feature
<222> LOCATION: (255)..(255)
<223> OTHER INFORMATION: unknown nucleotide

<400> SEQUENCE: 34

| tcccgccccg | cancgacacg | ggcgaccgca | agcagnacta | caacatcctg | agcacgctgg | 60 |
| ggctgcgacc | ctcgaccacc | gactgcgaca | tcgtgcgccg | cgcctgcgag | agcgtgtcta | 120 |
| cgcgcgctgc | gcacatgtgc | tcggcggggc | tggcgggcgt | catcaaccgc | atgcgcgaga | 180 |
| gccgcagcga | ggacgtaatg | cgcatcactg | tgggcgtgga | tggctccgtg | tacaagctgc | 240 |
| accccaggtg | agccngcccc | gctctctccc | tggtaaagtg | gggcccaaaa | agcgcgcgct | 300 |
| ccaaggttcc | ttgcggttcc | caagctccaa | gat | | | 333 |

<210> SEQ ID NO 35
<211> LENGTH: 147
<212> TYPE: DNA
<213> ORGANISM: Artificial sequence
<220> FEATURE:
<223> OTHER INFORMATION: Exon 1c PCR amplification product

<400> SEQUENCE: 35

| actctcctct | gaactcgggc | ctcacatggc | caactgctac | ttggaacaaa | tcgcccttg | 60 |
| gctggcagat | gtgttaacat | gcccagacca | agatcccaac | tcccacaacc | caactcccag | 120 |
| gtcagatgga | acctcttctt | cccaggc | | | | 147 |

<210> SEQ ID NO 36
<211> LENGTH: 149
<212> TYPE: DNA
<213> ORGANISM: Homo sapiens
<220> FEATURE:
<221> NAME/KEY: misc_feature
<222> LOCATION: (12)..(12)
<223> OTHER INFORMATION: unknown nucleotide

<400> SEQUENCE: 36

| actctcctct | gnaactcggg | cctcacatgg | ccacactgct | acttggaaca | aatcgcccct | 60 |
| tggctggcag | atgtgttaac | atgcccagac | caagatccca | actcccacaa | cccaactccc | 120 |

-continued

```
aggtcagatg gaacctcttc ttcccaggc                                149
```

<210> SEQ ID NO 37
<211> LENGTH: 253
<212> TYPE: DNA
<213> ORGANISM: Artificial sequence
<220> FEATURE:
<223> OTHER INFORMATION: Exon 7 PCR amplification product

<400> SEQUENCE: 37

```
aggcggcagg aaccaggccc tactccgggg cagtgcagct ctcgctgaca gtcccccga    60 cctccacccc aggcacgggc tgcaatgcct gctacatgga ggagatgcag aatgtggagc   120
tggtggaggg ggacgagggc cgcatgtgcg tcaataccga gtggggcgcc ttcggggact   180
ccggcgagct ggacgagttc ctgctggagt atgaccgcct ggtggacgag agctctgcaa   240
accccggtca gca                                                     253
```

<210> SEQ ID NO 38
<211> LENGTH: 253
<212> TYPE: DNA
<213> ORGANISM: Homo sapiens

<400> SEQUENCE: 38

```
aggcggcagg aaccaggccc tactccgggg cagtgcagct ctcgctgaca gtcccccga    60 cctccacccc aggcacgggc tgcaatgcct gctacatgga ggagatgcag aatgtggagc   120
tggtggaggg ggacgagggc cgcatgtgcg tcaataccga gtggggcgcc ttcggggact   180
ccggcgagct ggacgagttc ctgctggagt atgaccgcct ggtggacgag agctctgcaa   240
accccggtca gca                                                     253
```